(12) United States Patent
Akiba et al.

(10) Patent No.: US 9,717,408 B2
(45) Date of Patent: Aug. 1, 2017

(54) OPHTHALMOLOGIC IMAGING APPARATUS FOR STIMULATED EYE

(71) Applicant: KABUSHIKI KAISHA TOPCON, Tokyo (JP)

(72) Inventors: Masahiro Akiba, Toda (JP); Yasufumi Fukuma, Wako (JP); Hiroshi Akiyama, Souka (JP); Hisashi Tsukada, Hachioji (JP); Eiichi Yanagi, Saitama (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 70 days.

(21) Appl. No.: 14/655,440

(22) PCT Filed: Dec. 4, 2013

(86) PCT No.: PCT/JP2013/082646
§ 371 (c)(1),
(2) Date: Jun. 25, 2015

(87) PCT Pub. No.: WO2014/103647
PCT Pub. Date: Jul. 3, 2014

(65) Prior Publication Data
US 2015/0320308 A1    Nov. 12, 2015

(30) Foreign Application Priority Data

Dec. 27, 2012 (JP) ................................ 2012-286377

(51) Int. Cl.
*G06K 9/00* (2006.01)
*A61B 3/10* (2006.01)
(Continued)

(52) U.S. Cl.
CPC ............ *A61B 3/102* (2013.01); *A61B 3/0025* (2013.01); *A61B 3/09* (2013.01); *A61B 3/1173* (2013.01); *A61B 3/12* (2013.01); *A61B 3/14* (2013.01)

(58) Field of Classification Search
None
See application file for complete search history.

(56) References Cited

U.S. PATENT DOCUMENTS 8,025,401 B2 * 9/2011 Rathjen ................ A61B 3/1005
351/205
8,931,903 B2 * 1/2015 Inoue .................... A61B 3/102
351/221
(Continued)

FOREIGN PATENT DOCUMENTS

JP    2005-103069    4/2005
JP    2008-503271    2/2008
(Continued)

OTHER PUBLICATIONS

International Search Report dated Jan. 28, 2014, issued for International Application No. PCT/JP2013/082646.
(Continued)

*Primary Examiner* — Tahmina Ansari
(74) *Attorney, Agent, or Firm* — Procopio, Cory, Hargreaves & Savitch LLP

(57) ABSTRACT

An ophthalmologic imaging apparatus includes: a first optical system that applies an accommodation stimulus to a subject's eye; a tomographic image forming unit that includes a second optical system that splits light from a light source into signal light and reference light, and detects interference light between the signal light having travelled via the subject's eye and the reference light, and creates a tomographic image of the subject's eye based on a detection result of the interference light; and an analyzer that com-
(Continued)

pares a first tomographic image with a second tomographic image to acquire change information indicating a change in a tissue of the subject's eye due to an accommodation stimulus change. The first and second tomographic images are respectively created by the tomographic image forming unit for the subject's eye, to which first and second accommodation stimuli are respectively applied by the first and second optical systems.

19 Claims, 10 Drawing Sheets

(51) Int. Cl.
    *A61B 3/00*     (2006.01)
    *A61B 3/14*     (2006.01)
    *A61B 3/12*     (2006.01)
    *A61B 3/117*     (2006.01)
    *A61B 3/09*     (2006.01)

(56) References Cited

U.S. PATENT DOCUMENTS

2005/0280777 A1    12/2005    Dai
2010/0004538 A1*    1/2010    Eilers ........................ A61B 8/10
                                                600/444
2011/0032480 A1*    2/2011    Rathjen ................ A61B 3/1005
                                                351/206
2012/0083667 A1    4/2012    Isogai et al.
2015/0320308 A1*    11/2015    Akiba .................... A61B 3/102
                                                382/131

FOREIGN PATENT DOCUMENTS

| JP | 2009-66325 | 4/2009 |
| JP | 2011-212432 | 10/2011 |
| JP | 2012-075640 | 4/2012 |

OTHER PUBLICATIONS

Satoh Nobuyuki, Shimizu Kimiya, Igarashi Akihito, Kamiya Kazutaka (Univ. Kitasato School of Medicine, Kanagawa, JPN), GOTO Atsushi (Canon Inc., Tokyo, JPN), Ohbayashi Kohji (Univ. Kitasato, Kanagawa, JPN), Accommodative changes in human eye observed by Kitasato anterior segment optical coherence tomography, Jpn J Ophthalmol,vol. 57 No. 1, Nov. 21, 2012, p. 113-119 (http://rd.springer.com/article/10. 1007/s10384-012-0208-6).

* cited by examiner

OPHTHALMOLOGIC IMAGING APPARATUS FOR STIMULATED EYE

The present application is a National Stage entry of PCT/JP2013/082646, filed on Dec. 4, 2013, which claims priority from Japanese Patent Application No. 2012-286377, filed Dec. 27, 2012, the contents of which are incorporated herein by reference in their entirety.

TECHNICAL FIELD

The present invention relates to an ophthalmologic imaging apparatus.

BACKGROUND TECHNOLOGY

The ophthalmologic imaging apparatus is used to capture an image of a subject's eye. Examples of the ophthalmologic imaging apparatus include slit lamps, fundus cameras, scanning laser ophthalmoscopes (SLO), and the like.

In recent years, there has been proposed an apparatus that uses optical coherence tomography (OCT) for imaging the eye fundus and the anterior eye segment (see, for example, Patent Document 1). The OCT apparatus is advantageous in that it can acquire high-resolution images and also tomographic images. The tomographic images of the eye are subjected to various analysis processes to be used as diagnostic materials (see, for example, Patent Document 2).

[Patent Document 1] Japanese Unexamined Patent Application Publication No. 2011-212432

[Patent Document 2] Japanese Unexamined Patent Application Publication No. 2009-66325

SUMMARY OF THE INVENTION

Problems to be Solved by the Invention

The accommodation function is extremely important in the vision. The accommodation function is a function to adjust the focus by changing the refractive power of the eye according to the distance to the object. The crystalline lens, zonule of Zinn and ciliary body contribute to the change in the refractive power of the eye. The crystalline lens is a convex lens with variable refractive power. The zonule of Zinn is a tissue that couples the lens with the ciliary body. The ciliary body is a muscle tissue. For near vision, the ciliary muscle contracts, the zonular fibers relax, and accordingly the lens becomes thicker, which increase the refractive power. On the other hand, for far vision, the ciliary muscle relaxes, then the zonular fibers are stretched, and the lens consequently becomes flatter, which reduce the refractive power.

With the conventional technologies, it has been difficult to determine, in terms of structure, whether the tissues involved in the accommodation function having such a mechanism are functioning properly. For example, it has been difficult to figure out whether the ciliary body, which is a muscle tissue, has a sufficient ability to contract and relax.

Besides, even when the ciliary body is functioning properly, if the flexibility of the lens declines due to a cataract or the like, or if an implanted intraocular lens is not located in a proper position, the focus cannot be suitably adjusted. In the conventional technologies, it has been difficult to specify whether such a problem of the accommodation function is caused by the ciliary body, the zonule of Zinn, or the lens or the intraocular lens. For example, with the conventional technologies, it is difficult to determine whether the accommodative dysfunction is caused by a decline in the function of the ciliary muscle due to aging or the like, the relaxation of the zonule of Zinn, or a decline in the shape-changing function (flexibility) of the lens.

An objective of the present invention is to provide a technology whereby the accommodation function of the eye can be suitably judged.

Means of Solving the Problems

An ophthalmologic imaging apparatus of an embodiment includes: a first optical system configured to apply an accommodation stimulus to a subject's eye; a tomographic image forming unit including a second optical system configured to split light from a light source into signal light and reference light, and detect interference light between the signal light having travelled via the subject's eye and the reference light, the tomographic image forming unit configured to create a tomographic image of the subject's eye based on a detection result of the interference light; and an analyzer configured to compare a first tomographic image with a second tomographic image to acquire change information indicating a change in a predetermined tissue of the subject's eye due to a change of the accommodation stimulus, wherein the tomographic image forming unit is configured to create the first tomographic image of the subject's eye to which a first accommodation stimulus is being applied by the first optical system, and the second tomographic image of the subject's eye to which a second accommodation stimulus is being applied.

MODES FOR CARRYING OUT THE INVENTION

Embodiments of ophthalmologic imaging apparatuses related to the present invention are explained in detail with reference to the accompanying drawings.

[Exterior Structure]

Figure 1:
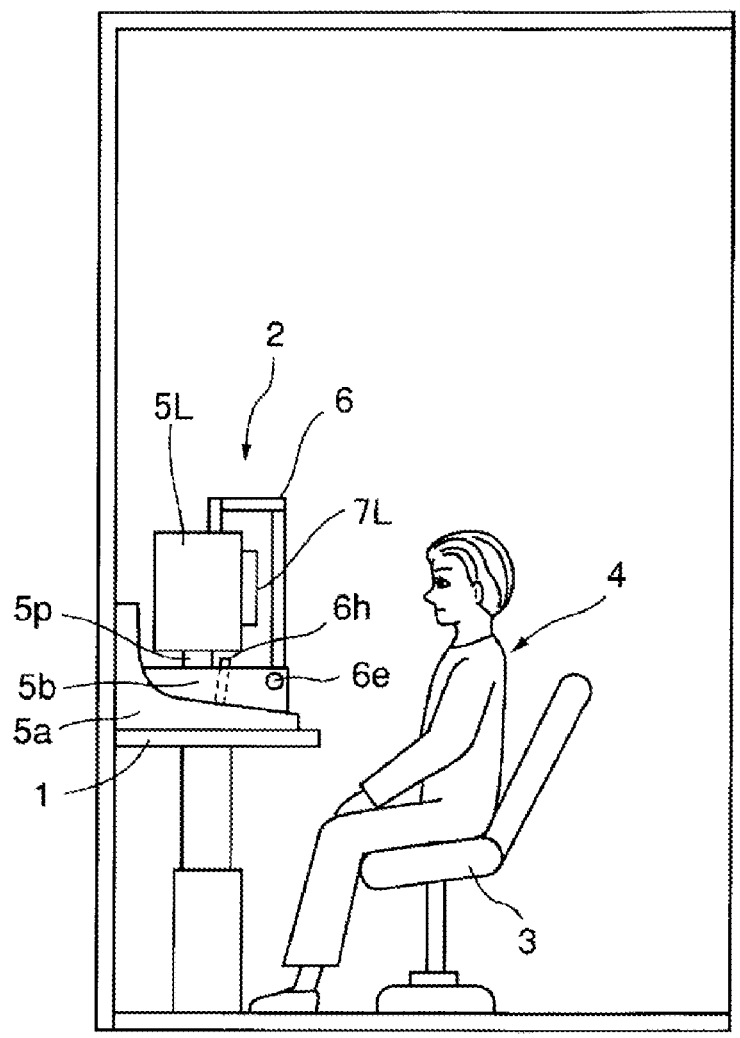
FIG. 1 is a schematic diagram illustrating an example of a configuration of an ophthalmologic imaging apparatus according to an embodiment.
Figure 2:
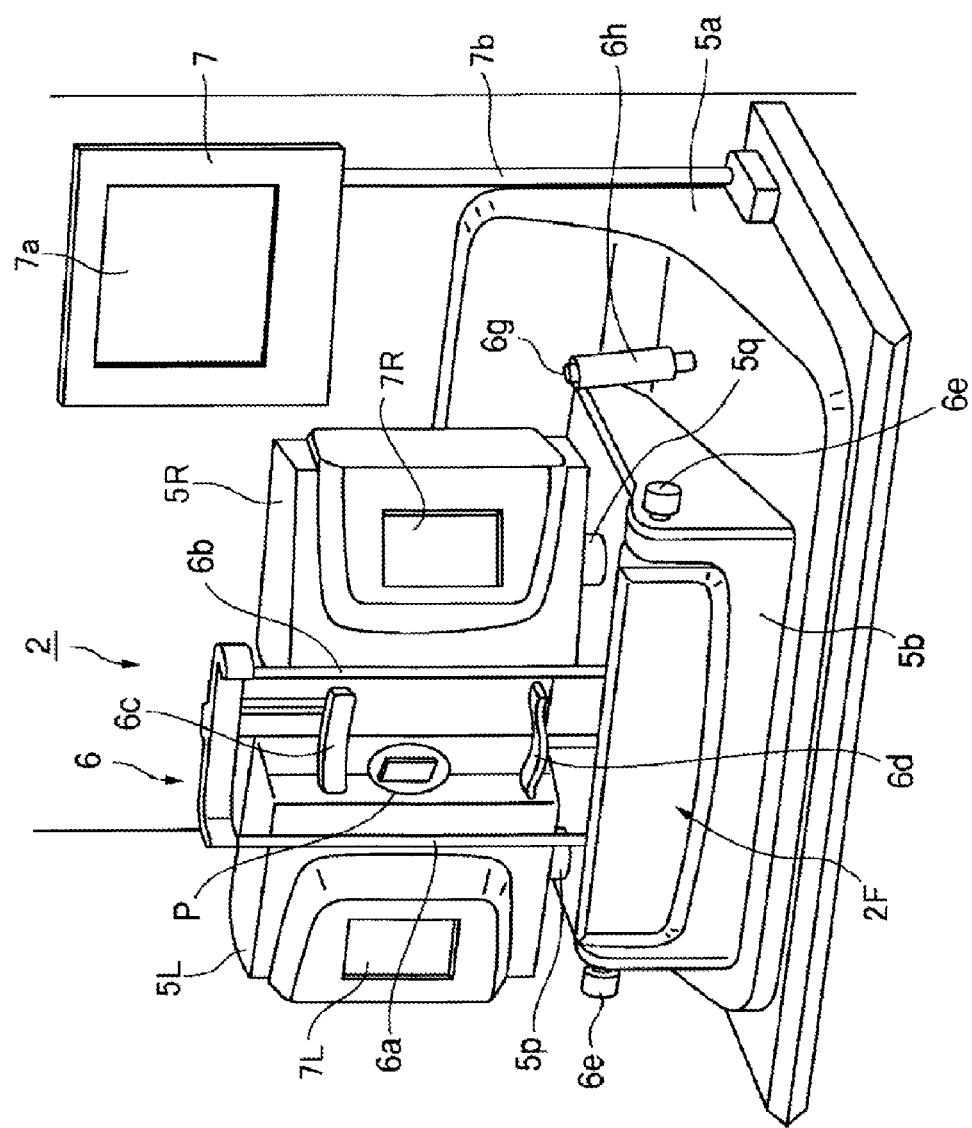
FIG. 2 is a schematic diagram illustrating an example of a configuration of an ophthalmologic imaging apparatus according to an embodiment.

FIGS. 1 and 2 illustrate an example of the appearance of an ophthalmologic imaging apparatus according to an embodiment. An ophthalmologic imaging apparatus 2 is placed on an optometry table 1, the height of which is adjustable. A subject 4 is seated in an optometry chair 3. The subject 4 faces toward the front 2F of the ophthalmologic imaging apparatus 2. The ophthalmologic imaging apparatus 2 includes a base 5a, a drive mechanism 5b, a pair of left and right bodies 5L and 5R, and a face holder 6. The bodies 5L and 5R are supported by struts 5p and 5q, respectively.

The face holder 6 includes a pair of left and right struts 6a and 6b. The struts 6a and 6b support a forehead rest 6c. The forehead rest 6c is movable in the longitudinal direction. The face holder 6 further includes a jaw rest 6d. The jaw rest 6d is moved by a knob 6e in the vertical direction.

The drive mechanism 5b includes an XYZ drive mechanism and a rotary drive mechanism. The XYZ drive mechanism drives the struts 5p and 5q in the horizontal direction (X direction), the vertical direction (Y direction), and the longitudinal direction (Z direction). The XYZ drive mechanism includes, for example, an actuator such as a pulse motor and a power transmission mechanism such as a feed screw. The rotary drive mechanism performs swing operation and tilt operation. The swing operation is intended to rotate the struts 5p and 5q about their respective axes (i.e., in the horizontal direction). The tilt operation is intended to tilt the struts 5p and 5q. The rotary drive mechanism includes, for example, an actuator such as a pulse motor and a power transmission mechanism such as a gear. The drive mechanism 5b thus configured moves the bodies 5L and 5R in the X, Y and Z directions and the rotation direction.

The base 5a is provided with a lever 6h for operation input to the ophthalmologic imaging apparatus 2. A button 6g is arranged on the top of the lever 6h. Although not illustrated, an operating unit may be arranged on the back side of the ophthalmologic imaging apparatus 2.

On the base 5a, a strut 7b is erected to support a display 7. Various types of information are displayed on a screen 7a of the display 7. The front surfaces of the left and right bodies 5L and 5R are respectively provided with displays 7L and 7R. The left and right displays 7L and 7R display, for example, the anterior eye image of the left eye and the right eye of the subject 4, respectively. The displays 7, 7L and 7R are flat panel displays such as liquid crystal displays. Although not illustrated, there may be a display provided on the back side of the ophthalmologic imaging apparatus 2.

[Configuration of Optical System]

Figure 3:
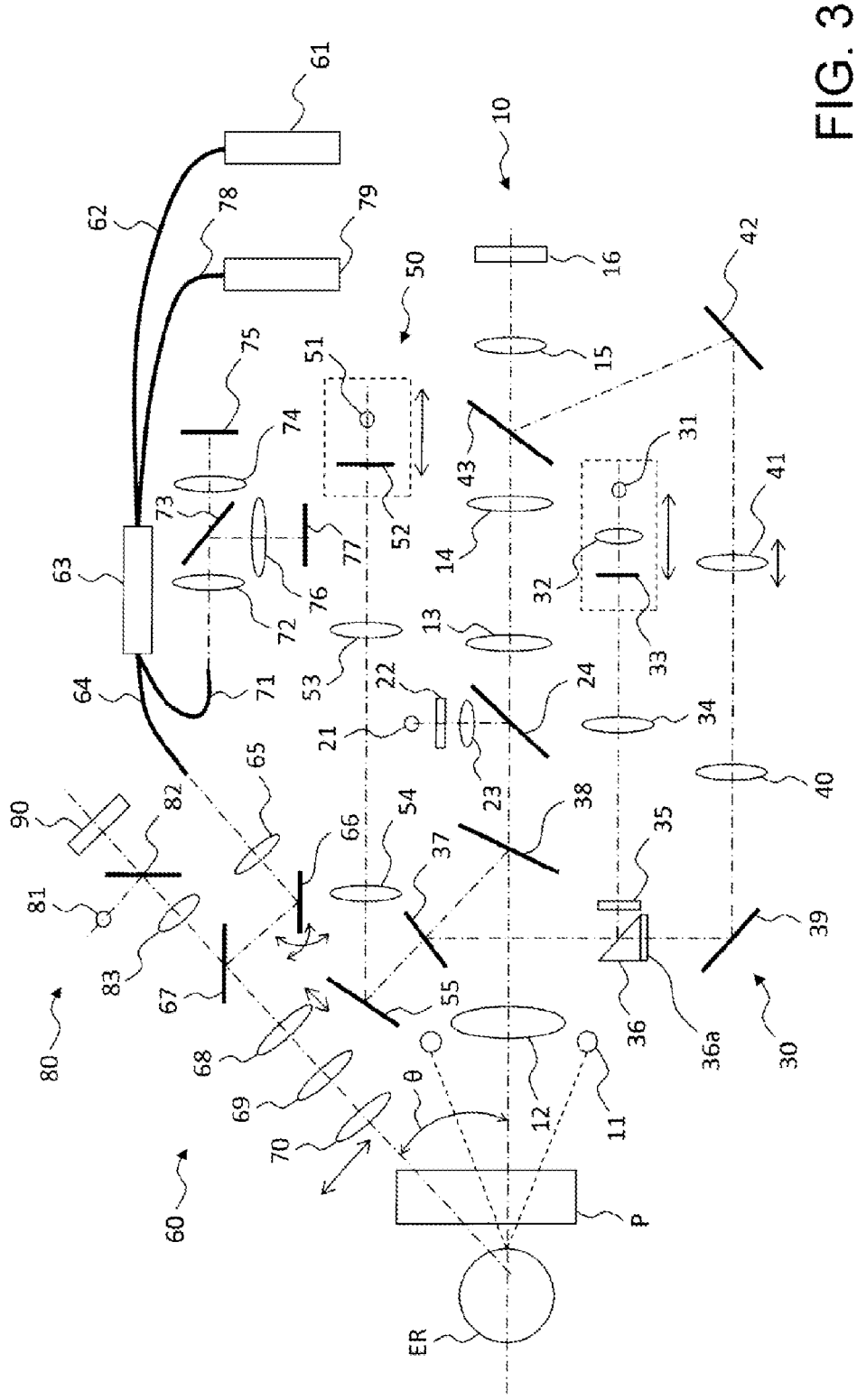
FIG. 3 is a schematic diagram illustrating an example of a configuration of an ophthalmologic imaging apparatus according to an embodiment.

A description is given of an optical system provided on the left and right bodies 5L and 5R. FIG. 3 is a top view illustrating an example of an optical system provided on the right body 5R. The left body 5L is provided with an optical system that is symmetrical to the optical system of the right body 5R. Reference sign ER represents the right eye of the subject 4 (subject's right eye).

The body 5R is provided with an imaging optical system 10, a measurement optical system 30, a visual target projection optical system 50, an interference optical system 60, and a fixation optical system 80. In the example of FIG. 3, the optical axis of the imaging optical system 10, the measurement optical system 30 and the visual target projection optical system 50 is oriented in a different direction from the direction of the optical axis of the interference optical system 60 and the fixation optical system 80. The angle formed by these optical axes is represented by θ. The angle θ may be variable or fixed.

(Imaging Optical System 10)

The imaging optical system 10 is used to photograph the anterior segment of the subject's right eye ER. The imaging optical system 10 includes a prism P, anterior eye illumination light sources 11, an objective lens 12, relay lenses 13 and 14, an imaging lens 15, and an image pickup device 16.

The anterior eye illumination light sources 11 are arranged in a periphery of the optical axis of the imaging optical system 10, and output light for illuminating the anterior eye segment. The light output from the anterior eye illumination light sources 11 is irradiated to the subject's right eye ER via the prism P, and then is reflected by the anterior eye segment. The reflected light passes through the prism P, the objective lens 12, the relay lens 13, and the imaging lens 15, and is detected by the image pickup device 16. Note that the light reflected by the anterior eye segment is transmitted through beam splitters 38, 24 and 43 (described later) and guided to the image pickup device 16. An anterior eye image obtained by the image pickup device 16 is, for example, displayed on the display 7L.

The beam splitter 24 is obliquely arranged between the objective lens 12 and the relay lens 13. Light output from an alignment light source 21 passes through an alignment target aperture 22 and a lens 23, then is reflected by the beam splitter 24, and is projected onto the anterior segment of the subject's right eye ER via the objective lens 12 and the prism P. As in the conventional manner, based on an alignment target image depicted in the anterior eye image, the alignment of the imaging optical system 10 is performed for the subject's right eye ER.

(Measurement Optical System 30)

The measurement optical system 30 optically measures an optical property of the subject's right eye ER. The measurement optical system 30 of this embodiment measures the refractive power of the subject's right eye ER. The measurement optical system 30 includes a measurement light source 31, a collimating lens 32, a ring transparent plate 33, a relay lens 34, a ring-shaped diaphragm 35, a perforated prism 36, beam splitters 37 and 38, the objective lens 12, the prism P, a reflective mirror 39, a relay lens 40, a movable lens 41, a reflective mirror 42, the beam splitter 43, the imaging lens 15, and the image pickup device 16.

Light output from the measurement light source 31 is collimated by the collimating lens 32, and becomes a light flux having a ring-shaped cross-section as passing through the ring transparent plate 33. The light travels through the relay lens 34 and the ring-shaped diaphragm 35, and is reflected by the perforated prism 36, then by the beam splitter 37, and by the beam splitter 38 to be irradiated to the subject's right eye ER via the objective lens 12 and the prism P.

The measurement light flux having a ring-shaped cross-section irradiated onto the subject's right eye ER is reflected by the fundus, and is output from the subject's right eye ER. At this time, the cross-sectional shape of the measurement light flux is deformed due to the influence of the eye optical system (cornea, lens, etc.).

The measurement light flux output from the subject's right eye ER travels through the prism P, the objective lens 12, the beam splitters 37 and 38, passes through a transparent plate 36a of the perforated prism 36, and is reflected by the reflective mirror 39. The light flux then passes through the relay lens 40 and the movable lens 41, and is reflected by the reflective mirror 42 and the beam splitter 43 to be detected by the image pickup device 16 via the imaging lens 15. By analyzing the size and shape of the cross section of the detected measurement light flux, the spherical degree, astigmatic degree, astigmatic axis, etc. of the subject's right eye ER are obtained. This process is performed in the conventional manner. In short, the ophthalmologic imaging apparatus 2 functions as a refractometer.

(Visual Target Projection Optical System 50)

The visual target projection optical system 50 presents a variety of visual targets to the subject's right eye ER. The visual target projection optical system 50 includes a target light source 51, a target plate 52, relay lenses 53 and 54, a reflective mirror 55, the beam splitter 38, the objective lens 12, and the prism P. The target plate 52 includes, for example, a turret plate or a transmissive liquid crystal display, and is configured to be capable of selectively positioning various visual targets, such as a fixation target and optotypes, with respect to the optical path. Light output from the target light source 51 passes through the above components of the visual target projection optical system 50, and is projected onto the fundus of the subject's right eye ER.

The target light source 51 and the target plate 52 are configured to be movable in the optical axis direction of the visual target projection optical system 50. This allows a change of the viewing distance of the subject's right eye ER to the visual target. That is, the visual target projection optical system 50 can be used to provide an accommodation stimulus to the subject's right eye ER.

(Interference Optical System 60)

The interference optical system 60 is used for optical coherence tomography (OCT) measurement of the subject's right eye ER. The interference optical system 60 includes a light source unit 61, an optical fiber 62, a fiber coupler 63, an optical fiber 64, a collimating lens 65, a galvanometer scanner 66, a beam splitter 67, a focusing lens 68, a relay lens 69, a condenser lens 70, the prism P, an optical fiber 71, a collimating lens 72, a beam splitter 73, a lens 74, a first reference mirror 75, a lens 76, a second reference mirror 77, an optical fiber 78, and a detector 79.

Any type of OCT measurement may be used in this embodiment. If swept-source OCT is employed, a wavelength-swept light source capable of modulating output wavelength at a high speed is used as the light source unit 61, and an optical detector such as a balanced photo detector is used as the detector 79. If spectral domain OCT is employed, a broadband light source (low-coherence light source) is used as the light source unit 61, and a spectroscope for detecting spectra is used as the detector 79.

The galvanometer scanner 66 includes, for example, two reflective mirrors and actuators for changing the orientations of the respective reflective mirrors. The galvanometer scanner 66 scans the subject's right eye ER with light (signal light) passing therethrough.

The condenser lens 70 is removably arranged on the optical path of the interference optical system 60. For example, the condenser lens 70 is arranged on the optical path when an image of the subject's right eye ER is to be captured, while it is retracted from the optical path when the intraocular distance (axial length etc.) is to be measured.

The first reference mirror 75 is arranged in a position conjugate to a first site of the subject's right eye ER. The first site is a site to be subjected to OCT measurement and may be, for example, the cornea, the ciliary body, the crystalline lens, or the like. The first reference mirror 75 and the lens 74 are integrally movable in the optical axis direction.

The second reference mirror 77 is arranged in a position conjugate to a second site of the subject's right eye ER. The second site is a site to be subjected to OCT measurement and may be, for example, the retina, the choroid, or the like. The second reference mirror 77 and the lens 76 are integrally movable in the optical axis direction.

Light output from the light source unit 61 is guided to the fiber coupler 63 through the optical fiber 62. The fiber coupler 63 divides the light into two parts.

Light (signal light) guided by the fiber coupler 63 to the optical fiber 64 is collimated by the collimating lens 65, and directed to a different direction by the galvanometer scanner 66. The light is then reflected by the beam splitter 67, and passes through the focusing lens 68, the relay lens 69, (the condenser lens 70), and the prism P to be irradiated to the subject's right eye ER. The backscattered light of the signal light from the subject's right eye ER is guided through the same path in the opposite direction, and returns to the fiber coupler 63.

Light (reference light) guided by the fiber coupler 63 to the optical fiber 71 is collimated by the collimating lens 72 and guided to the beam splitter 73. Component transmitted through the beam splitter 73 (first reference light) is condensed by the lens 74, reflected by the first reference mirror 75, collimated by the lens 74, and returns to the beam splitter 73. Meanwhile, component reflected by the beam splitter 73 (second reference light) is condensed by the lens 76, reflected by the second reference mirror 77, collimated by the lens 76, and returns to the beam splitter 73. The first reference light and the second reference light (collectively referred to as "reference light") combined by the beam splitter 73 return to the fiber coupler 63 via the collimating lens 72 and the optical fiber 71. The optical path of the reference light is referred to as "reference optical path".

The fiber coupler 63 makes the signal light having travelled via the subject's right eye ER interfere with the reference light having travelled through the reference optical path. The interference light includes information on the site (the ciliary body etc.) of the subject's right eye ER conjugate to the first reference mirror 75 and information on the site (the retina etc.) of the subject's right eye ER conjugate to the second reference mirror 77. The interference light is led to the detector 79 through the optical fiber 78. In the case of swept-source OCT, the detector 79 detects the intensity of the interference light. In the case of spectral domain OCT, the detector 79 detects distribution of spectra of the interference light.

Although not illustrated, the interference optical system 60 is provided with an attenuator and a polarization controller. The attenuator is located, for example, on the optical fiber 71 to adjust the amount of the reference light guided to the optical fiber 71. The polarization controller applies a stress to, for example, the looped optical fiber 71 from the outside to adjust the polarization state of the reference light guided to the optical fiber 71. In addition to them, the interference optical system 60 may be provided with various types of known devices applicable to OCT measurement.

(Fixation Optical System 80)

The fixation optical system 80 presents a fixation target to the subject's right eye ER. The fixation optical system 80 includes a fixation light source 81, a beam splitter 82, a collimating lens 83, the focusing lens 68, the relay lens 69, and the prism P. Light output from the fixation light source 81 is reflected by the beam splitter 82, and collimated by the collimating lens 83. The light is transmitted through the beam splitter 67, and travels through the focusing lens 68, the relay lens 69, and the prism P to be projected onto the fundus of the subject's right eye ER.

Behind the beam splitter 82 of the fixation optical system 80 is arranged an imaging device 90. The imaging device 90 is used to capture an image of the anterior segment of the subject's right eye ER. Since the optical axis of the imaging optical system 10 and that of the interference optical system 60 are oriented in different directions, the imaging optical system 10 and the imaging device 90 photograph the anterior segment of the subject's right eye ER from different directions.

[Configuration of Control System]

Figure 4:
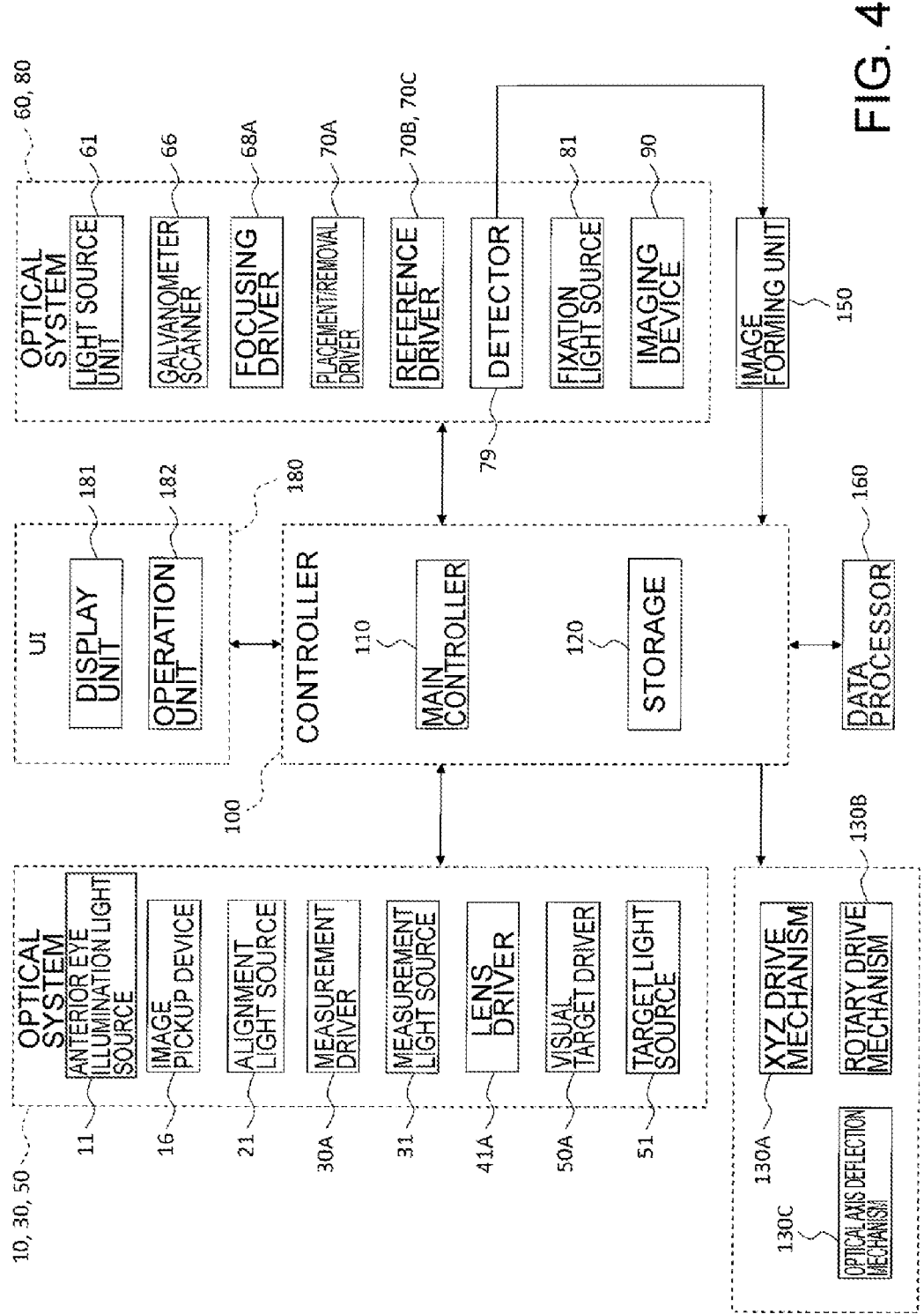
FIG. 4 is a schematic diagram illustrating an example of a configuration of an ophthalmologic imaging apparatus according to an embodiment.
Figure 5:
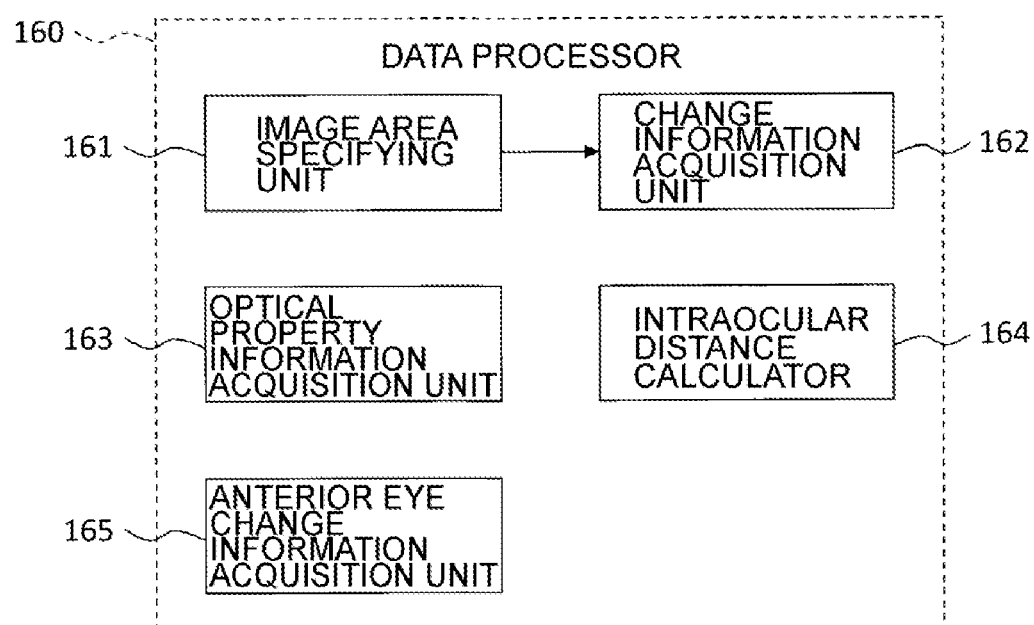
FIG. 5 is a schematic diagram illustrating an example of a configuration of an ophthalmologic imaging apparatus according to an embodiment.

FIGS. 4 and 5 illustrate an example of the configuration of the control system of the ophthalmologic imaging apparatus 2.

(Controller 100)

The control system of the ophthalmologic imaging apparatus 2 is configured centering on the controller 100. The controller 100 includes, for example, a processor, a storage device, a communication interface, and the like. The storage device stores computer programs and data for control/calculation operation. The controller 100 includes a main controller 110 and a storage 120.

(Main Controller 110)

The main controller 110 controls each unit of the ophthalmologic imaging apparatus 2. For example, the main controller 110 controls the operation of the anterior eye illumination light sources 11, the image pickup device 16, the alignment light source 21, the measurement light source 31, the target light source 51, the light source unit 61, the galvanometer scanner 66, the detector 79, the fixation light source 81, and the imaging device 90 illustrated in FIG. 3. Although not illustrated, the main controller 110 controls the attenuator and the polarization controller.

The main controller 110 controls the movement of the optical element. For example, the main controller 110 controls a measurement driver 30A to move the measurement light source 31, the collimating lens 32, and the ring transparent plate 33 in the optical axis direction. The measurement driver 30A includes an actuator such as a pulse motor and a power transmission mechanism. The main controller 110 controls a lens driver 41A to move the movable lens 41 in the optical axis direction. The lens driver 41A includes an actuator such as a pulse motor and a power transmission mechanism. The main controller 110 controls a visual target driver 50A to move the target light source 51 and the target plate 52 in the optical axis direction. The visual target driver 50A includes an actuator such as a pulse motor and a power transmission mechanism. The main controller 110 controls a focusing driver 68A to move the focusing lens 68 in the optical axis direction. The focusing driver 68A includes an actuator such as a pulse motor and a power transmission mechanism. The main controller 110 controls a placement/removal driver 70A to place/remove the condenser lens 70 with respect to the optical path. The placement/removal driver 70A includes an actuator such as a solenoid and a power transmission mechanism. The main controller 110 controls a reference driver 70B to move the lens 74 and the first reference mirror 75 in the optical axis direction. Similarly, the main controller 110 controls a reference driver 70C to move the lens 76 and the second reference mirror 77 in the optical axis direction. Each of the reference drivers 70B and 70C includes an actuator such as a pulse motor and a power transmission mechanism.

The main controller 110 controls the movement of the optical system. For example, the main controller 110 controls an XYZ drive mechanism 130A provided in the drive mechanism 5b to move the bodies 5L and 5R in three dimensions. The XYZ drive mechanism 130A includes an actuator such as a pulse motor and a power transmission mechanism. The main controller 110 controls a rotary drive mechanism 130B to rotationally move the bodies 5L and 5R around the struts 5p and 5q, respectively. The main controller 110 controls the rotary drive mechanism 130B to tilt the struts 5p and 5q, thereby tilting the bodies 5L and 5R. The rotary drive mechanism 130B includes an actuator such as a pulse motor and a power transmission mechanism. The main controller 110 controls an optical axis deflection mechanism 130C to relatively change the direction of the optical axis (first optical axis) of the imaging optical system 10, the measurement optical system 30, and the visual target projection optical system 50, and the direction of the optical axis (second optical axis) of the interference optical system 60 and the fixation optical system 80. The optical axis deflection mechanism 130C changes either or both the direction of the first optical axis and that of the second optical axis. This changes the angle θ illustrated in FIG. 3. The optical axis deflection mechanism 130C includes an actuator such as a pulse motor and a power transmission mechanism.

The main controller 110 performs writing of data to the storage 120 as well as reading of data from the storage 120.

(Storage 120)

The storage 120 stores various types of data. Examples of the data stored in the storage 120 include image data of an anterior eye image, image data of an OCT image, measurement data of a subject's eye, and subject's eye information. The subject's eye information includes information about a subject such as patient ID and name, and information about the subject's eye such as identification information of the left eye/right eye.

(Image Forming Unit 150)

Having detected interference light in OCT measurement, the detector 79 outputs a signal. This signal is fed to the image forming unit 150. The image forming unit 150 creates image data of a two-dimensional tomogram of the subject's right eye ER based on the signal from the detector 79. As in the conventional manner, this image forming process includes noise removal (noise reduction), filtering, fast Fourier transform (FFT), and the like. The image forming unit 150 includes, for example, a hardware circuit and/or a processor to execute software for image formation. Incidentally, in this specification, "image data" and "image" may sometimes be identified with each other.

(Data Processor 160)

The data processor 160 performs various types of data processing. For example, the data processor 160 applies various types of image processing and analysis processing to an OCT image and an anterior eye image. Examples of the processing include luminance correction and dispersion correction. The data processor 160 creates a three-dimensional image based on the two-dimensional tomogram formed by the image forming unit 150. The data processor 160 includes a processor to execute software for data processing. The data processor 160 is an example of "analyzer".

The data processor 160 includes an image area specifying unit 161, a change information acquisition unit 162, an optical property information acquisition unit 163, an intraocular distance calculator 164, and an anterior eye change information acquisition unit 165.

The ophthalmologic imaging apparatus 2 applies an accommodation stimulus to the subject's eye. The accommodation stimulus refers to visual information provided to the subject's eye to exert arbitrary accommodation force. The ophthalmologic imaging apparatus 2 applies an accommodation stimulus by the visual target projection optical system 50. More specifically, the ophthalmologic imaging apparatus 2 moves the target light source 51 and the target plate 52 by the visual target driver 50A to guide the focus of the subject's eye to a predetermined position.

In this embodiment, an examination is performed as follows. First, OCT measurement is performed while a first accommodation stimulus is being applied to the subject's eye to acquire a first tomographic image of the eye. Then, OCT measurement is performed while a second accommodation stimulus different from the first one is being applied to acquire a second tomographic image of the eye. The first accommodation stimulus and the second accommodation stimulus correspond to different focal positions. For example, the first accommodation stimulus corresponds to a far focal position, while the second accommodation stimulus corresponds to a near focal position. The data processor 160 performs the following processing to obtain a change in the predetermined tissue of the subject's eye caused by a change of the accommodation stimulus. The information indicating such a change is referred to as "change information". The predetermined tissue where a change is to be detected may be, for example, tissue related to the accommodation function such as the ciliary body, the crystalline lens, and the zonule of Zinn.

(Image Area Specifying Unit 161)

The image area specifying unit 161 analyzes the first tomographic image to specify an image area corresponding to the predetermined tissue. The image area specifying unit 161 also analyzes the second tomographic image to specify an image area corresponding to the predetermined tissue. When such processing is performed automatically, the image area specifying unit 161 distinguishes an image area of the predetermined tissue from other image areas based on the pixel values (luminance values) of the first tomographic image. The processing includes, for example, threshold processing, pattern matching, and the like.

Part of the processing may be performed manually. In this case, the main controller 110 displays a tomographic image on a display unit 181. The user observes the tomographic image displayed and figures out an image area corresponding to the predetermined tissue, thereby designating the image area through an operation unit 182. The image area may be specified by, for example, inputting a plurality of points on the contour of the image area corresponding to the predetermined tissue using a pointing device such as a mouse. The image area specifying unit 161 finds a closed curve that connects the points input. This closed curve is, for example, a spline curve or a Bezier curve. An area surrounded by the closed curve is the image area of interest. For another example, the contour may be input by using a pointing device.

(Change Information Acquisition Unit 162)

The change information acquisition unit 162 compares the image area (first image area) specified in the first tomographic image with the image area (second image area) specified in the second tomographic image, and thereby obtains change information indicating a change in the morphology of the predetermined tissue.

A change in shape may be cited as an example of morphological change of a predetermined tissue. In this case, the change information acquisition unit 162 calculates a predetermined evaluation value based on each of the first image area and the second image area, and compares the evaluation values to obtain the change information. Specifically, for example, the change information acquisition unit 162 calculates evaluation values such as thickness, size (area, volume, etc.), perimeter, and the like of the predetermined tissue based on the contour of each of the first image area and the second image area. Then, the change information acquisition unit 162 obtains a value (the difference, ratio, etc.) indicating the difference between the evaluation value of the first image area and that of the second image area to use it as the change information. Further, a change of the evaluation value per unit accommodation amount may be obtained by dividing the value indicating the difference by the amount of a change in the accommodation stimulus (i.e., expected accommodation amount). Besides, a statistical value such as an average value and variation may be obtained by performing the above examination a plurality of times. This is effective for evaluating the ciliary body and the crystalline lens. If the zonule of Zinn formed of a fibrous tissue is the predetermined tissue, for example, a wire model of an image area corresponding to the zonule of Zinn may be obtained to compare the shape. Alternatively, two (or more) feature points of the predetermined tissue may be detected to obtain a change in the shape based on the distance(s) between the feature points.

As another example of the morphological change of the predetermined tissue may be cited a change in the density of tissue that constitutes the predetermined tissue. This example is applicable to, for example, the ciliary body. The ciliary body is muscle tissue consisting of a number of muscle fibers. The change information acquisition unit 162 analyzes each of the first image area and the second image area to specify a number of partial areas corresponding to the muscle fibers. Then, the change information acquisition unit 162 acquires the number of partial areas existing in an area of a predetermined area in the first image area, and the number of partial areas existing in the area in the second image area. This process is performed by labeling, for example. Further, the change information acquisition unit 162 obtains a value indicating the difference (variance, ratio, etc.) between these numbers to use it as change information. The change information indicates a change in the density of the muscle fibers due to the contraction or relaxation of the muscle tissue. Note that, by dividing the value representing the difference between the above numbers by the amount of a change in the accommodation stimulus (i.e., expected accommodation amount), expected density change per unit accommodation amount may be obtained. Besides, a statistical value such as an average value and variation of the density variation may be obtained by performing the above examination a plurality of times.

(Optical Property Information Acquisition Unit 163)

The optical property information acquisition unit 163 analyzes the optical property of the subject's eye obtained by the measurement optical system 30. The measurement optical system 30 measures the subject's eye to which the first accommodation stimulus is being applied to acquire a first measurement value, and also measures the subject's eye to which the second accommodation stimulus is being applied to acquire a second measurement value. These measurements are performed in parallel with or at a different time from the OCT measurement. The optical property information acquisition unit 163 acquires information indicating a change in the optical property of the subject's eye caused by a change of the accommodation stimulus based on the first measurement value and the second measurement value acquired. The information is referred to as "optical property information".

In this embodiment, the measurement optical system 30 functions as a refractometer for measuring the refractive power of the subject's eye. The optical property information acquisition unit 163 obtains the optical property information that indicates a change in the accommodation amount for the subject's eye due to a change of the accommodation stimulus based on the first measurement value and the second measurement of the refractive power of the subject's eye. This process is performed to calculate the difference between the first measurement value and the second measurement value. Note that the actual accommodation amount per expected unit accommodation amount may be obtained by dividing the difference between the two measurement values by the amount of a change in the accommodation stimulus (i.e., expected accommodation amount). Besides, a statistical value such as an average value and variation may be obtained by performing the above examination a plurality of times.

While this embodiment describes the measurement of the refractive power of the subject's eye, other optical properties of the subject's eye may be measured. For example, the aberrations of the subject's eye may be measured. As an example of the technology for the aberration measurement may be cited a wavefront sensor as described in JP 2001-275972 of the present applicant. The wavefront sensor irradiates the fundus of the subject's eye with a light flux from a point light source, and analyzes the distribution of a plurality of point images obtained by detecting the reflected light by an area sensor through a Hartmann plate to determine the aberrations of various orders. With such a wavefront sensor, as well as the spherical degree and astigmatic degree, higher order aberrations can be measured. The optical property information acquisition unit 163 acquires the optical property information indicating a change in the aberrations of the subject's eye due to a change of the accommodation stimulus with respect to the aberration of each order based on the first measurement value and the second measurement value.

(Intraocular Distance Calculator 164)

The intraocular distance calculator 164 calculates the distance between arbitrary sites of the subject's eye based on information acquired by OCT measurement. Such distance is referred to as "intraocular distance". Although the intraocular distance may be calculated by any method, this embodiment describes the following two methods.

The first intraocular distance calculation method is based on the optical path length difference between the first reference light and the second reference light. Here, the first reference light is reference light travelling via the first reference mirror 75, while the second reference light is reference light travelling via the second reference mirror 77. As described above, the first reference mirror 75 is moved by the reference driver 70B together with the lens 74 in the optical axis direction, and the second reference mirror 77 is moved by the reference driver 70C together with the lens 76 in the optical axis direction. Thereby, the optical path length of the first reference light and that of the second reference light are changed individually.

Since the reference drivers 70B and 70C operate under the control of the main controller 110, the main controller 110 can recognize the amount of a change in the optical path length made by each of the reference drivers 70B and 70C. For example, if the reference drivers 70B and 70C each includes a pulse motor as the actuator, the main controller 110 can calculate the amount a change in the optical path length based on the operation amount of the pulse motor per one pulse (i.e., unit moving distance of the reference mirror by the pulse motor) and the number of pulses transmitted to the pulse motor. Besides, the main controller 110 can find the positions of the first reference mirror 75 and the second reference mirror 77, that is, the optical path length of the first reference light and that of the second reference light, based on the control histories (pulse transmission histories) relative to the reference drivers 70B and 70C.

The reference drivers 70B and 70C are an example of "optical path length changing unit". Note that although the optical path length of the reference light is changed in this embodiment, the optical path length of the signal light may be changed. The optical path length of the signal light can be changed by using, for example, a movable corner cube. In addition, both the optical path length of the reference light and that of the signal light may be changed.

In this method, a tomographic image of the first site of the subject's eye and a tomographic image of the second site are acquired by OCT measurement. The two OCT measurements are performed in parallel or at different times. In this embodiment, by virtue of the two reference mirrors 75 and 77, the OCT measurements of different sites of the subject's eye can be performed in parallel. Incidentally, if there are three or more reference mirrors and an optical system which splits the optical path of the reference light according to the number of the reference mirrors, the OCT measurements of three or more sites can be performed simultaneously.

The OCT measurement of the first site is performed so that the backscattered light of the signal light from the first site and the first reference light interfere effectively with each other. In other words, the OCT measurement of the first site is performed such that the optical path length between the fiber coupler 63 and the first site (the optical path length of the signal light) and the optical path length between the fiber coupler 63 and the first reference mirror 75 (the optical path length of the first reference light) match each other. That is, in the OCT measurement of the first site, the first reference mirror 75 is located in a position substantially conjugate to the first site.

Similarly, the OCT measurement of the second site is performed so that the backscattered light of the signal light from the second site and the second reference light interfere effectively with each other. In other words, the OCT measurement of the second site is performed such that the optical path length between the fiber coupler 63 and the second site (the optical path length of the signal light) and the optical path length between the fiber coupler 63 and the second reference mirror 77 (the optical path length of the second reference light) match each other. That is, in the OCT measurement of the second site, the second reference mirror 77 is located in a position substantially conjugate to the second site.

The intraocular distance calculator 164 calculates the distance between the first site and the second site based on the optical path lengths of the first reference light when the tomographic image of the first site is acquired, and the optical path length of the second reference light when the tomographic image of the second site is acquired. This process is accomplished by calculating the difference between the optical path length of the first reference light and that of the second reference light.

One example of this method is capable of obtaining the axial length of the subject's eye. In this case, the first site is set to the anterior surface of the cornea, and the second site is set to the surface of the fundus. That is, the first reference mirror 75 is located in a position conjugate to the anterior surface of the cornea, and the second reference mirror 77 is located in a position conjugate to the surface of the fundus. In this example, a cornea tomographic image depicting the cornea and a fundus tomographic image depicting the fundus are obtained. The intraocular distance calculator 164 calculates the axial length of the subject's eye based on the position of the first reference mirror 75 in the OCT measurement for acquiring the cornea tomographic image (i.e., the optical path length of the first reference light), and the position of the second reference mirror 77 in the OCT measurement for acquiring the fundus tomographic image (i.e., the optical path length of the second reference light). Thus, this method can measure a relatively long intraocular distance.

Another example of this method is capable of obtaining the anterior chamber depth. In this case, the first site is set to the posterior surface of the cornea, and the second site is set to the anterior surface of the crystalline lens. That is, the first reference mirror 75 is located in a position conjugate to the posterior surface of the cornea, and the second reference mirror 77 is located in a position conjugate to the anterior surface of the lens. In this example, a cornea tomographic image depicting the cornea and a lens tomographic image depicting the lens are obtained. The intraocular distance calculator 164 calculates the anterior chamber depth based on the position of the first reference mirror 75 in the OCT measurement for acquiring the cornea tomographic image (i.e., the optical path length of the first reference light), and the position of the second reference mirror 77 in the OCT measurement for acquiring the lens tomographic image (i.e., the optical path length of the second reference light).

The second intraocular distance calculation method is intended to find the intraocular distance by analyzing a single tomographic image. In this analysis, first, an image area corresponding to the first site depicted in the tomographic image, and an image area corresponding to the second site are specified. As with the image area specifying unit 161, this process is performed automatically or in part manually. The intraocular distance calculator 164 calculates the distance between the specified two image areas. This process is performed based on a scale which is set in advance for the tomographic image. Besides, this process may include a process of counting the number of pixels existing between the two image areas.

One example of this method is capable of obtaining the anterior chamber depth. In this example, either one of the first reference mirror 75 or the second reference mirror 77 is used for OCT measurement (here, it is assumed that the first reference mirror 75 is used). The first reference mirror 75 is located in a position which is conjugated with an arbitrary position of the anterior segment. For example, the first reference mirror 75 is located at a position conjugated with a position between the posterior surface of the cornea and the anterior surface of the lens. The intraocular distance calculator 164 calculates the depth of the anterior chamber of the subject's eye by calculating the distance between the image area corresponding to the posterior surface of the cornea and the image area corresponding to the anterior surface of the lens.

(Anterior Eye Change Information Acquisition Unit 165)

The ophthalmologic imaging apparatus 2 has a function of photographing the anterior eye segment. The anterior eye photography is performed by using the imaging optical system 10 or the imaging device 90. In this embodiment, a first anterior eye image is captured by photographing the subject's eye to which the first accommodation stimulus is being applied. In addition, a second anterior eye image is captured by photographing the subject's eye to which the second accommodation stimulus is being applied. The anterior eye photography is performed in parallel with or at a different time from the OCT measurement. The anterior eye change information acquisition unit 165 compares the first anterior eye image and the second anterior eye image, and thereby obtains information indicating a change in a predetermined tissue of the anterior eye segment caused along with a change of the accommodation stimulus. This information is referred to as "anterior eye change information".

The iris is an example of the predetermined tissue of the anterior eye segment to be analyzed. First, the anterior eye change information acquisition unit 165 specifies an image area corresponding to the predetermined tissue depicted in the first anterior eye image, and an image area corresponding to the predetermined tissue depicted in the second anterior eye image. As with the image area specifying unit 161, this process is performed automatically or in part manually. Further, the anterior eye change information acquisition unit 165 compares the two image areas specified to obtain morphological changes (changes in pupil diameter, iris pattern, etc.) between the two image areas. Besides, based on a change of the elliptical shape of the pupil (ellipticity, orientation, etc.), a change in the direction of the visual line of the subject's eye (change in the eye axis direction) can be found.

(User Interface 180)

The user interface 180 is a man-machine interface used to provide information to the examiner and/or the subject, and is also used for operation and information input by the examiner and/or the subject. The user interface 180 includes the display unit 181 and the operation unit 182.

(Display Unit 181)

The display unit 181 includes the displays 7, 7L and 7R, and the display arranged on the back side of the ophthalmologic imaging apparatus 2 mentioned above. If a computer is connected to the ophthalmologic imaging apparatus 2, the display unit 181 may include a display of the computer. The display unit 181 displays information under the control of the main controller 110.

(Operation Unit 182)

The operation unit 182 is used for information input and the operation of the ophthalmologic imaging apparatus 2. The operation unit 182 includes the lever 6h and the button 6g mentioned above, and the operation unit on the back side of the ophthalmologic imaging apparatus 2. If a computer is connected to the ophthalmologic imaging apparatus 2, the operation unit 182 may include manipulation or input devices of the computer. The main controller 110 performs control in response to a signal from the operation unit 182.

The display unit 181 and the operation unit 182 need not be configured as individual devices. For example, like a touch panel, a device with integrated functions of display and operation may be employed.

[Operation]

Figure 6:
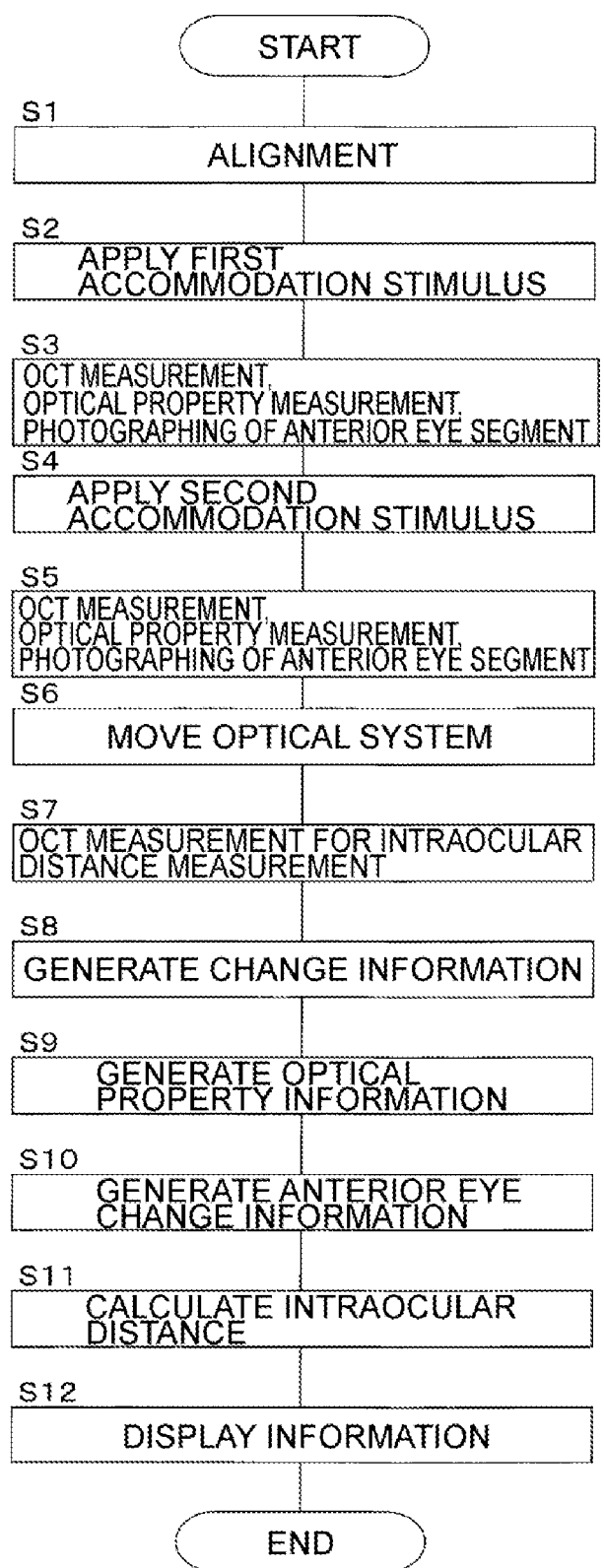
FIG. 6 is a flowchart showing an example of the operation of an ophthalmologic imaging apparatus according to an embodiment.

A description is given of an example of the operation of the ophthalmologic imaging apparatus 2. FIG. 6 illustrates an example of the operation of the ophthalmologic imaging apparatus 2. Here, an example is described in which the subject's right eye ER is examined.

(S1: Alignment)

First, an alignment of the optical system is performed with respect to the subject's right eye ER. Specifically, first, the main controller 110 turns on the anterior eye illumination light sources 11 and the alignment light source 21, and starts the operation of the image pickup device 16. Thus, an anterior eye image of the subject's right eye ER where an alignment target image is projected is obtained. The main controller 110 displays the anterior eye image on the display unit 181. The user adjusts the position of the optical system with reference to the position of the alignment target image reflected in the anterior eye image as in the conventional manner to align it with the subject's right eye ER. Incidentally, if the main controller 110 adjusts the position of the optical system by analyzing the position of the alignment target image, the alignment can be made automatically.

When an accommodation stimulus is applied also to the subject's left eye, the alignment of the optical system for the subject's left eye is performed in the same manner.

Figure 7:
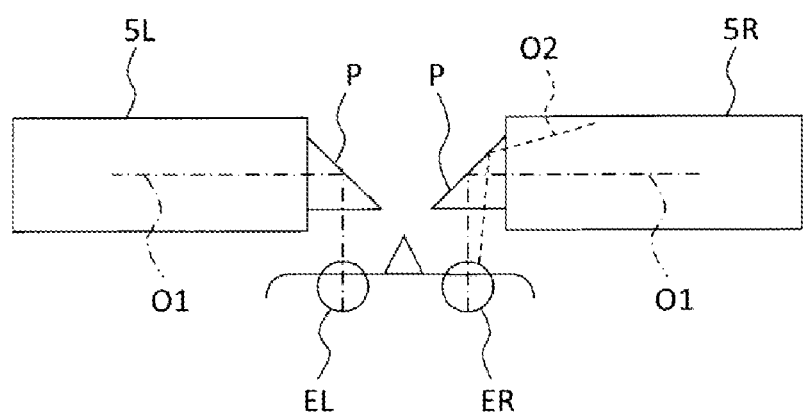
FIG. 7 is a schematic diagram for explaining an example of the operation of an ophthalmologic imaging apparatus according to an embodiment.

FIG. 7 illustrates an example of a state where the alignment is completed. Reference sign O1 represents the optical axis (the first optical axis) of the imaging optical system 10, the measurement optical system 30, and the visual target projection optical system 50. Reference sign O2 represents the optical axis (the second of the optical axis) of the interference optical system 60 and the fixation optical system 80. The main controller 110 controls the XYZ drive mechanism 130A and the rotary drive mechanism 130B based on the anterior eye image acquired by the imaging optical system 10 to match the first optical axis O1 with the axis of the subject's right eye ER to accomplish the alignment of the right body 5R.

As illustrated in FIG. 3, the second optical axis O2 is at an angle θ with respect to the first optical axis O1. The alignment of the second optical axis O2 may be performed in a state where the position of the first optical axis O1 is fixed. To perform this alignment, for example, the main controller 110 controls the optical axis deflection mechanism 130C based on live OCT images obtained through repetitive OCT measurements and/or the anterior eye image captured by the imaging device 90.

When an accommodation stimulus is applied also to the subject's left eye EL, the main controller 110 performs the alignment of the first optical axis O1 of the left body 5L in the same manner as in the case of the right body 5R. When the OCT measurement of the subject's left eye EL is also conducted, the alignment of the second optical axis (not illustrated) of the left body 5L is performed in the same manner as in the case of the right body 5R.

Figure 8:
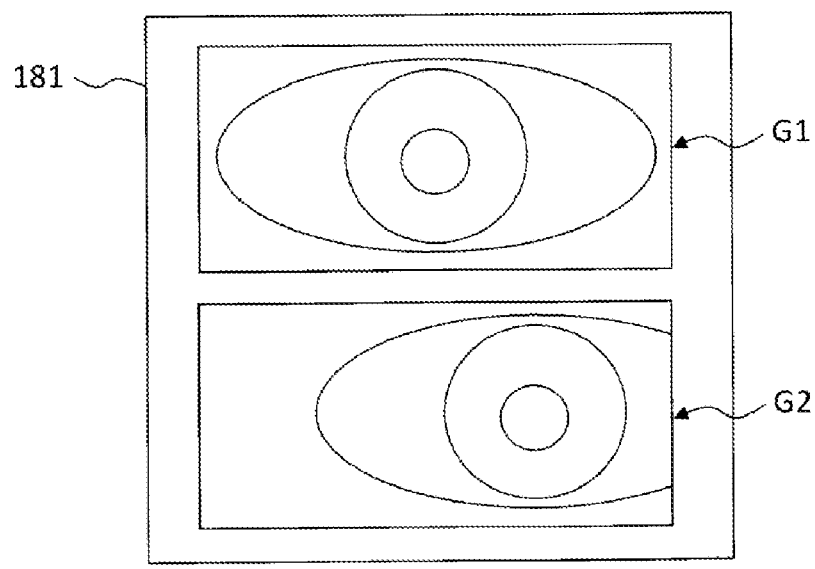
FIG. 8 is a schematic diagram for explaining an example of the operation of an ophthalmologic imaging apparatus according to an embodiment.

The main controller 110 displays the anterior eye image thus obtained on the display unit 181. FIG. 8 illustrates an example of the display of the anterior eye image when the alignment is completed. The main controller 110 displays an anterior eye image G1 acquired by the imaging optical system 10, and an anterior eye image G2 acquired by the imaging device 90 as moving imaged on the display unit 181. Since the first optical axis O1 is substantially aligned with the axis of the subject's right eye ER, the anterior eye image G1 is an image obtained by photographing the subject's right eye ER from the front. On the other hand, since the second optical axis O2 is inclined by an angle θ with respect to the first optical axis O1, the anterior eye image G2 is an image obtained by photographing the subject's right eye ER at a diagonal angle.

Figure 9:
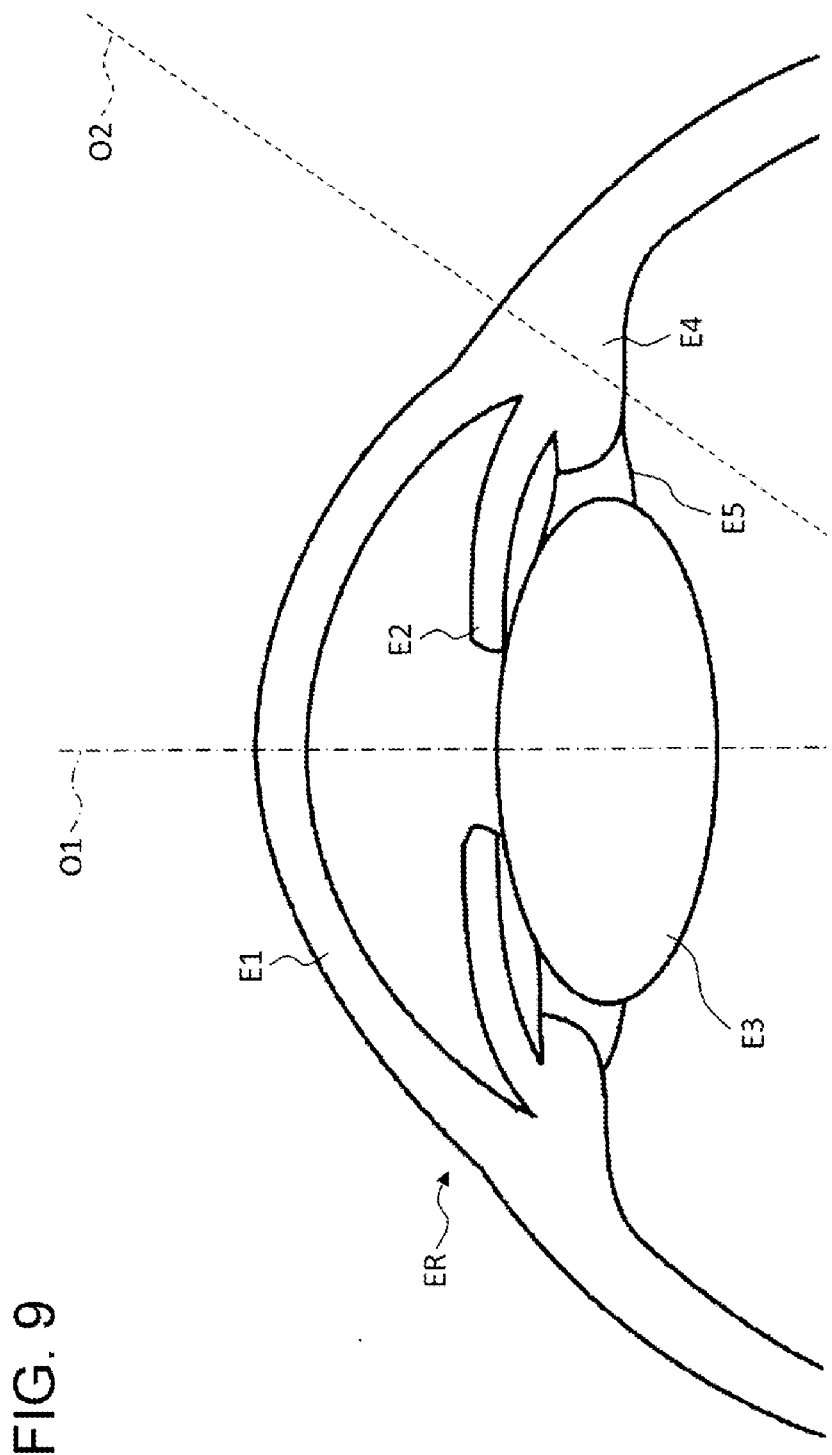
FIG. 9 is a schematic diagram for explaining an example of the operation of an ophthalmologic imaging apparatus according to an embodiment.

FIG. 9 illustrates an example of the positional relationship between the first optical axis O1 and the second optical axis O2 after the alignment is completed. FIG. 9 is a cross-sectional view of the subject's right eye ER. Reference sign E1 represents the cornea. Reference sign E2 represents the iris. Reference sign E3 represents the crystalline lens. Reference sign E4 represents the ciliary body. Reference sign E5 represents the zonule of Zinn. The first optical axis O1 is arranged in a location passing through the vertex of the cornea E1, passing through the hole surrounded by the iris E2 (that is, the pupil), and passing through the vertex of the lens E3. The second optical axis O2 that is inclined by an angle θ with respect to the first optical axis O1 is arranged in a position passing through the ciliary body E4.

(S2: Application of the First Accommodation Stimulus)

When the alignment is completed, the main controller 110 applies the first accommodation stimulus to the subject's right eye ER (and the subject's left eye). Specifically, the main controller 110 turns on the target light source 51, and also controls the visual target driver 50A to place the target light source 51 and the target plate 52 each at a position corresponding to the first accommodation stimulus. The positions of the target light source 51 and the like corresponding to the first accommodation stimulus are set in advance.

(S3: OCT Measurement, Optical Property Measurement, Photographing of the Anterior Segment of the Subject's Eye)

While the first accommodation stimulus is being applied to the subject's right eye ER (and the subject's left eye), the main controller 110 performs OCT measurement, optical property measurement, and photographing of the anterior eye segment. Note that all or two of the three operations may be performed in parallel, or they may be performed at different times. In this stage, the condenser lens 70 is arranged on the optical path of the interference optical system 60.

Described below is the OCT measurement. First, the main controller 110 controls the reference driver 70B to arrange the first reference mirror 75 and the lens 74 each in a position corresponding to the ciliary body E4. This process is performed with reference to, for example, live OCT images obtained through repetitive OCT measurements. Upon completion of the positioning of the first reference mirror 75, the main controller 110 controls the light source unit 61 and the galvanometer scanner 66 to perform the OCT measurement in an area of the subject's right eye ER containing the ciliary body. The detector 79 detects the interference light between the signal light that has travelled via the subject's right eye ER and the reference light that has travelled via the first reference mirror 75. The image forming unit 150 creates a tomographic image based on a signal output from the detector 79. The tomographic image illustrates the morphology of the ciliary body E4 in a state where the first accommodation stimulus is being applied. The main controller 110 stores the acquired tomographic image in the storage 120. This tomographic image is used as the first tomographic image.

Described below is the optical property measurement. First, the main controller 110 turns on the measurement light source 31. A measurement light flux output from the measurement light source 31 is reflected by the fundus of the subject's right eye ER and detected by the image pickup device 16. The main controller 110 sends a signal output from the image pickup device 16 to the optical property information acquisition unit 163. This signal includes information indicating the size and shape of the cross section of the measurement light flux detected by the image pickup device 16. The optical property information acquisition unit 163 analyzes the signal, and thereby calculates the spherical degree, astigmatic degree, and the astigmatic axis of the subject's right eye ER. The main controller 110 stores the measurement values of the optical properties calculated in the storage 120. Such a measurement value indicates the optical property value of the subject's right eye ER to which the first accommodation stimulus is being applied, and is used as the first measurement value.

Described below is photographing of the anterior eye segment. If the anterior eye illumination light sources 11 are continuously on from step 1, the image pickup device 16 feeds signals to the controller 100 at predetermined time intervals (frame rate). The main controller 110 stores image data based on a signal input at a predetermined timing (any time while the first accommodation stimulus is being applied) in the storage 120. This image data represents the morphology of the anterior segment of the subject's right eye ER to which the first accommodation stimulus is being applied, and is used as the image data of the first anterior eye image.

If the anterior eye illumination light sources 11 are not lit at least at a point immediately before the photographing of the anterior eye segment, the main controller 110 turns on the anterior eye illumination light sources 11 to photograph the anterior eye segment, and stores image data of the first anterior eye image thus obtained in the storage 120.

(S4: Application of the Second Accommodation Stimulus)

Upon completion of the OCT measurement, the optical property measurement, and the photographing of the anterior eye segment, the main controller 110 applies the second accommodation stimulus to the subject's right eye ER (and the subject's left eye). Specifically, the main controller 110 controls the visual target driver 50A to move the target light source 51 and the target plate 52 each arranged at a position corresponding to the first accommodation stimulus to a position corresponding to the second accommodation stimulus. The positions of the target light source 51 etc. corresponding to the second accommodation stimulus are set in advance.

(S5: OCT Measurement, Optical Property Measurement, Photographing of the Anterior Segment of the Subject's Eye)

While the second accommodation stimulus is being applied to the subject's right eye ER (and the subject's left eye), the main controller 110 performs OCT measurement, optical property measurement, and photographing of the anterior eye segment. These processes are performed in the same manner as in step 3. Thereby, a second tomographic image, a second measurement value, and a second anterior eye image are acquired for the subject's right eye ER to which the second accommodation stimulus is being applied. The information is stored in the storage 120.

(S6: Movement of the Optical System)

Figure 10:
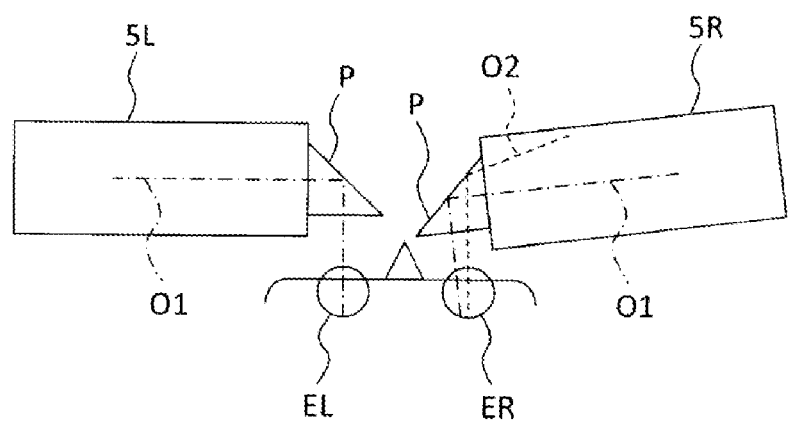
FIG. 10 is a schematic diagram for explaining an example of the operation of an ophthalmologic imaging apparatus according to an embodiment.

Upon completion of the OCT measurement, the optical property measurement, and the photographing of the anterior eye segment in step 5, the main controller 110 moves the optical system to a position for intraocular distance measurement. Specifically, the main controller 110 controls the rotary drive mechanism 130B such that the optical axis (the second optical axis O2) of the interference optical system 60 matches the axis of the subject's right eye ER (see FIG. 10). This rotational movement of the optical system is intended to rotate the right body 5R by the angle θ. The main controller 110 controls the XYZ drive mechanism 130A to adjust the distance from the interference optical system 60 to the subject's right eye ER. The main controller 110 controls the placement/removal driver 70A to retract the condenser lens 70 from the optical path of the interference optical system 60.

(S7: OCT Measurement for Intraocular Distance Measurement)

After the optical system has been moved, the main controller 110 controls the reference driver 70B to place the first reference mirror 75 and the lens 74 each in a position corresponding to the first site of subject's right eye ER (e.g., the anterior surface of the cornea E1). The main controller 110 also controls the reference driver 70C to place the second reference mirror 77 and the lens 76 each in a position corresponding to the second site of the subject's right eye ER (e.g., the surface of the fundus). This process is performed with reference to, for example, live OCT images obtained by repetitive OCT measurements. In such OCT measurements, the fixation of the subject's right eye ER is made by the fixation light source 81.

Upon completion of the positioning of the first reference mirror 75 and the second reference mirror 77, the main controller 110 controls the light source unit 61 and the galvanometer scanner 66 to perform OCT measurement of the subject's right eye ER. The detector 79 detects the interference light between the reference light and the signal light having travelled via the subject's right eye ER. The interference light includes interference component (first interference component) of the signal light having travelled via the first site of the subject's right eye ER and the reference light having travelled via the first reference mirror 75, and the interference component (second interference component) of the signal light having travelled via the second site and the reference light having travelled via the second reference mirror 77.

The image forming unit 150 creates tomographic images based on signals output from the detector 79. In this operation example, the image forming unit 150 creates a cornea tomographic image illustrating the anterior surface of the corneal E1 based on the first interference component, and a fundus tomographic image illustrating the surface of the fundus based on the second interference component. The main controller 110 stores the cornea tomographic image and the fundus tomographic image thus acquired in the storage 120. Incidentally, the OCT measurement of the first site and the OCT measurement of the second site may be performed at different times.

Thus, the optical measurements for the subject's right eye ER are completed, and data processing takes place. Incidentally, the following steps 8 to 11 are performed in arbitrary order. In addition, two or more of these steps may be performed in parallel.

(S8: Generation of Change Information)

The data processor 160 generates change information indicating a change in a predetermined tissue (e.g., the ciliary body) of the subject's right eye ER due to a change of the accommodation stimulus. In this operation example, the change information indicates the difference between the morphology of the predetermined tissue to which the first accommodation stimulus is being applied and the morphology of the predetermined tissue to which the second accommodation stimulus is being applied.

As described below, step 8 includes two stages of processes. In the first stage, the image area specifying unit 161 analyzes the first tomographic images acquired in step 3 to specify a ciliary body area, and analyzes the second tomographic image acquired in step 5 to specify a ciliary body area. In the second stage, the change information acquisition unit 162 compares the ciliary body area in the first tomographic image and the ciliary body area in the second tomographic image, and thereby obtains the change information indicating a change in the morphology of the ciliary body E4 (shape, the density of muscle fibers, etc.). The main controller 110 stores the change information thus acquired in the storage 120.

(S9: Generation of Optical Property Information)

The data processor 160 generates optical property information that indicates a change in the optical property of the subject's right eye ER due to a change of the accommodation stimulus. In this operation example, the optical property information acquisition unit 163 obtains the optical property information indicating a change in the amount of accommodation of the subject's right eye ER caused by a change of the accommodation stimulus based on the first measurement value of the ocular refractive power obtained in step 3, and the second measurement value obtained in step 5. The main controller 110 stores the optical property information thus acquired in the storage 120.

(S10: Generation of Anterior Eye Change Information)

The data processor 160 generates anterior eye change information indicating a change in the predetermined tissue of the anterior segment of the subject's right eye ER due to a change of the accommodation stimulus. In this operation example, the anterior eye change information acquisition unit 165 obtains the anterior eye change information that indicates changes in the pupil diameter of the subject's right eye ER, in the iris pattern, in the direction of the visual line, and the like based on a first anterior eye image obtained in step 3 and a second anterior eye image obtained in step 5. The main controller 110 stores the anterior eye change information thus acquired in the storage 120.

(S11: Calculation of the Intraocular Distance)

The data processor 160 calculates the intraocular distance of the subject's right eye ER. In this operation example, the intraocular distance calculator 164 calculates the axial length of the subject's right eye ER, that is, the distance between the anterior surface of the cornea and the surface of the fundus based on the positions of the first reference mirror 75 and the second reference mirror 77 when the corneal tomographic image and the fundus tomographic image are obtained in step 7. The main controller 110 stores the intraocular distance calculated in the storage 120.

(S12: Display of Information)

The main controller 110 retrieves the information obtained in steps 8 to 11 from the storage 120 and displays it on the display unit 181. With this, the operation example is completed.

[Actions and Effects]

Described below are the actions and effects of the ophthalmologic imaging apparatus 2.

The ophthalmologic imaging apparatus 2 includes a first optical system, a tomographic image forming unit, and an analyzer. The first optical system includes the visual target projection optical system 50 configured to apply an accommodation stimulus to a subject's eye. The first optical system is an example of a stimulating unit for stimulating the subject's eye. The tomographic image forming unit includes the interference optical system 60. The interference optical system 60, which corresponds to a second optical system, splits light from a light source (the light source unit 61) into signal light and reference light, and detects interference light between the signal light having travelled via the subject's eye and the reference light. The tomographic image forming unit creates a tomographic image of the subject's eye based on a detection result of the interference light obtained by the interference optical system 60. The analyzer includes the data processor 160. The analyzer is configured to compare a first tomographic image of the subject's eye to which a first accommodation stimulus is being applied with a second tomographic image of the subject's eye to which a second accommodation stimulus is being applied, and thereby obtain change information indicating a change in a predetermined tissue of the subject's eye caused by a change of the accommodation stimulus.

The data processor 160 may include the image area specifying unit 161 and the change information acquisition unit 162. The image area specifying unit 161 analyzes the first tomographic image corresponding to the first accommodation stimulus and the second tomographic image corresponding to the second accommodation stimulus, and specifies image areas corresponding to the predetermined tissue of the subject's eye. The change information acquisition unit 162 compares the image area specified in the first tomographic image with the image area specified in the second tomographic image, and thereby obtains information indicating a change in the morphology of the predetermined tissue of the subject's eye as the above change information.

The change information acquisition unit 162 may acquire, as the change information, information indicating a change in the shape of the predetermined tissue of the subject's eye and/or a change in the density of tissues that constitute the predetermined tissue. Thereby, it is possible to figure out how the shape and/or density of the predetermined tissue change according to the accommodation stimulus.

When the ciliary body is used as the predetermined tissue, the following configuration may be applicable. The image area specifying unit 161 specifies a ciliary body area corresponding to the ciliary body as the image area. Then, the change information acquisition unit 162 compares the ciliary body area in the first tomographic image and the ciliary body area in the second tomographic image, and thereby obtains information indicating a change in the shape of the ciliary body of the subject's eye and/or a change in the density of the muscle fibers of the ciliary body as the change information. Thus, it is possible to figure out how the shape of the ciliary body and/or the density of muscle fibers change according to the accommodation stimulus.

When the ciliary body is used as the predetermined tissue, the application of the accommodation stimulus to the subject's eye and the OCT measurement of the ciliary body may be performed while the optical axis (first optical axis O1) of the first optical system and the optical axis (second optical axis O2) of the second optical system are oriented in different directions. Thereby, it is possible to suitably carry out the application of the accommodation stimulus and the OCT measurement of the ciliary body in parallel. In other words, while the accommodation stimulus is being applied from the front of the subject's eye, the OCT measurement can be suitably performed from the direction inclined with respect to the eye axis.

When the ciliary body is used as the predetermined tissue, there may be provided an optical system moving mechanism that relatively changes the direction of the first optical axis O1 and the direction of the second optical axis O2. In this embodiment, the optical axis deflection mechanism 130C corresponds to the optical system moving mechanism. Thereby, it is possible to suitably carry out the application of the accommodation stimulus and the OCT measurement of the ciliary body. In other words, while the accommodation stimulus is being applied from the front of the subject's eye, the OCT measurement can be suitably performed from the direction appropriate to the imaging of the ciliary body.

The predetermined tissue is not limited to the ciliary body. For example, the crystalline lens may be used as the predetermined tissue. It is then possible to use the following configuration. That is, the image area specifying unit 161 specifies a lens area corresponding to the lens as the image area. Then, the change information acquisition unit 162 compares the lens area in the first tomographic image and the lens area in the second tomographic image, and thereby acquires information indicating a change in the shape of the crystalline lens as the change information. This change information includes the thickness, the size (area, volume, etc.), the perimeter, etc. of the lens. Thereby, it is possible to figure out how the shape of the tissue of the lens or the like changes according to the accommodation stimulus. Note that in this embodiment, the lens refers not only to a biological lens but also to an artificial lens (i.e., intraocular lens).

The first optical system may include a pair of right and left optical systems that simultaneously apply the accommodation stimulus to the subject's left eye EL and right eye ER. Thereby, as compared with the case of applying the accommodation stimulus only to one of the subject's eyes, the accommodation can be suitably induced. In the case of applying the accommodation stimulus to both the eyes, the positions of the pair of left and right optical systems may be adjusted such that the subject's left and right eyes are congested. In this case, the convergence angle may be changed according to the accommodation stimulus. As a specific example, a first convergence angle related to the viewing distance corresponding to the first accommodation stimulus and a second convergence angle related to the viewing distance corresponding to the second accommodation stimulus may be obtained in advance so that the first and second convergence angles can be switched for use depending on a change of the accommodation stimulus.

The first optical system may include a measurement optical system configured to optically measure the optical properties of the subject's eye. In this embodiment, the measurement optical system 30 measures the subject's eye to which the first accommodation stimulus is being applied and thereby obtains first measurement values of the optical properties. Further, the measurement optical system measures the subject's eye to which the second accommodation stimulus is being applied and thereby obtains second measurement values of the optical properties. The optical property information acquisition unit 163 of the data processor 160 acquires optical property information indicating a change in the optical properties due to a change of the accommodation stimulus based on the first measurement values and the second measurement values. Thus, it is possible to figure out how the optical properties of the subject's eye change according to the accommodation stimulus.

The measurement optical system may measure the refractive power of the subject's eye as the optical properties. In this case, the optical property information acquisition unit 163 can acquire the optical property information that indicates a change in the amount of accommodation of the subject's eye due to a change of the accommodation stimulus based on the first and second measurement values of the refractive power. Thus, it is possible to figure out how the refractive power of the subject's eye changes according to the accommodation stimulus.

The measurement optical system may measure the aberration of the subject's eye as the optical properties. In this case, the optical property information acquisition unit 163 can obtain the optical property information that indicates a change in the aberration of the subject's eye due to a change of the accommodation stimulus based on the first and second measurement values of the aberration. Thus, it is possible to figure out how the aberration of the subject's eye changes according to the accommodation stimulus.

The second optical system may include an optical path length changing unit configured to change the length of the optical path of the signal light and/or the length of the optical path of the reference light. In this embodiment, the interference optical system 60 is provided with the reference driver 70B (70C) for changing the optical path length of the reference light. The tomographic image forming unit acquires a tomographic image of the first site and that of the second site of the subject's eye. The intraocular distance calculator 164 of the data processor 160 calculates the distance between the first site and the second site based on the optical path length when the tomographic image of the first site is acquired, and the optical path length when the tomographic image of the second site is acquired. Thus, it is possible to determine the distance between the first site and the second site of the subject's eye.

The anterior surface of the cornea may be used as the first site, while the surface of the fundus may be used as the second site. In this case, the intraocular distance calculator 164 obtains the axial length of the subject's eye.

The intraocular distance calculator 164 may be configured to analyze a single tomographic image of the subject's eye acquired by the tomographic image forming unit to calculate the distance between the first site and the second site depicted in this tomographic image. Thus, it is possible to determine the distance between the first site and the second site of the subject's eye.

The posterior surface of the cornea may be used as the first site, while the anterior surface of the crystalline lens may be used as the second site. In this case, the anterior chamber depth of the subject's eye can be obtained by the intraocular distance calculator 164.

The first optical system may include an imaging optical system configured to photograph the anterior segment of the subject's eye. In this embodiment, the imaging optical system 10 and an optical system including the imaging device 90 correspond to the imaging optical system. The imaging optical system captures a first anterior eye image of the subject's eye to which the first accommodation stimulus is being applied, a second anterior eye image of the subject's eye to which the second accommodation stimulus is being applied. The data processor 160 compares the first anterior eye image with the second anterior eye image, and thereby acquires anterior eye change information indicating a change in the predetermined tissue of the anterior eye segment due to a change of the accommodation stimulus. Thus, it is possible to figure out how the predetermined tissue of the anterior eye segment varies depending on the accommodation stimulus.

With the ophthalmologic imaging apparatus 2 configured as above, it is possible to determine whether the tissue related to the accommodation function of the subject's eye is functioning properly based on a structural change of the subject's eye. For example, it is possible to figure out whether the ciliary body as a muscle tissue has a sufficient ability to contract and relax. Further, it is also possible to comprehensively determine if the ciliary body is functioning properly, if the flexibility of the lens is reduced by the cataract, if the implanted intraocular lens is placed in a proper position, and the like. Thus, it is possible to specify a cause for that the accommodation function is not acting favorably.

As described above, with the ophthalmologic imaging apparatus 2, it is possible to suitably judge the accommodation function of the subject's eye.

Described below is the usage of the ophthalmologic imaging apparatus 2 according to the embodiment. With the use of the ophthalmologic imaging apparatus 2 for treatment related to the accommodation function and the follow-up of surgery, it is possible to comprehensively judge a change of the accommodation function due to treatment, surgery, and the passage of time. Further, it is also possible to obtain a time-series change in the accommodation function.

The ophthalmologic imaging apparatus 2 may be used to measure the efficiency of rehabilitation and training. In this case, the visual target projection optical system 50 may present a visual target for subjective optometry, such as Landolt rings, to the subject's eye. Then, it is possible to obtain a time-series change in the result of the subjective optometry and in the result of accommodation function measurement.

The ophthalmologic imaging apparatus 2 may be used for the evaluation of accommodating intraocular lenses. The accommodating intraocular lens is an intraocular lens having accommodation functions. As an example of the evaluation of the accommodating intraocular lens, it is possible to evaluate whether the accommodating intraocular lens implanted is functioning properly according to the movement of the ciliary body or the like. Besides, it is also possible to determine whether the ciliary body or the like of the subject's eye has a sufficient capacity for the implantation of the accommodating intraocular lens before the transplantation of the intraocular lens.

The embodiments described above are mere examples for embodying or carrying out the present invention, and therefore susceptible to several modifications and variations (omission, substitution, addition, etc.). Modifications described below come within the scope of the invention.

The wavelengths of light output from the light source unit 61 are arbitrarily set. For example, considering that the axial length measurement is performed by using OCT, a light source capable of outputting light having wavelengths of not more than 1.1 um may be used as the light source unit 61. Incidentally, the light source for OCT measurement intended to obtain a tomographic image, and the light source for OCT measurement intended to measure the intraocular distances may be separately provided.

In the above embodiment, an example is described in which an accommodation stimulus is applied to the subject's eye by using a visual target; however, the method of applying the accommodation stimulus to the subject's eye is not limited to this. For example, electrical stimulation, ultrasonic stimulation, or light stimulation may be applied to the subject's eye. The electrical stimulation is applied by, for example, applying an electrode to a site to be stimulated. The ultrasonic stimulation is applied by, for example, irradiating a site to be stimulated with ultrasonic waves by using an ultrasonic transducer. The light stimulation is applied by using a light source.

The site of the subject's eye to be stimulated is not limited to the sites related to the accommodation function (lens, zonule of Zinn, ciliary body). For example, a stimulus may be applied to the retina.

Such an ophthalmologic imaging apparatus includes a stimulating unit, a tomographic image forming unit, and an analyzer. The stimulating unit applies a stimulus to the subject's eye. The stimulus includes the presentation of a visual target, electrical stimulation, ultrasonic stimulation, light stimulation, and the like. The stimulating unit includes a means for presenting a visual target to the subject's eye, a means for applying electrical stimulation to the subject's eye, a means for applying ultrasound stimulation to the subject's eye, a means for applying light stimulation to the subject's eye, and the like. The tomographic image forming unit includes an optical system configured to split light from a light source into signal light and reference light, and detect interference light between the signal light having travelled via the subject's eye and the reference light. The tomographic image forming unit creates a tomographic image of the subject's eye based on a detection result of the interference light. The analyzer is configured to compare a first tomographic image of the subject's eye to which a first accommodation stimulus is being applied by the stimulating unit with a second tomographic image of the subject's eye to which a second accommodation stimulus is being applied, both of which are obtained by the tomographic image forming unit, and thereby obtain change information indicating a change in a predetermined tissue of the subject's eye caused by a change of the accommodation stimulus. With this ophthalmologic imaging apparatus, it is possible to judge a change of the subject's eye due to a change of the stimulus.

In the above embodiment, although the change information is acquired based on the tomographic image of the subject's eye, it may be acquired based on data detected by the interference optical system in the OCT measurement, intermediate information from the detected data to the tomographic image, or information obtained from the tomographic image. For example, in the above embodiment, the change information may be obtained based on a signal output from the detector 79 of the interference optical system 60, the change information may also be obtained based on information (intermediate information from the signal to the tomographic image) acquired by the image forming unit 150 which has received the signal, and further, the change information may also be obtained based on information generated by the data processor 160 from the tomographic image. In addition, the change information may be obtained based on phase information acquired by OCT of phase detection type. In this case, it is possible to figure out a slight change in the subject's eye (a change of wavelength scale or less) caused by a change in the stimulus.

In the above embodiment, an example is described in particular detail in which two pieces of information corresponding to two stimulating conditions are compared to each other; however, this is not so limited. For example, the change information may be obtained from three or more pieces of information corresponding to three or more stimulating conditions. That is, by acquiring the i-th information (tomographic images etc.) on the subject's eye to which the i-th stimulus is being applied (i=1 to K), the change information may be obtained based on K pieces of information. Further, the change information may be obtained based on three or more pieces of information corresponding to two or more stimulating conditions. For example, the change information may be obtained based on information of the subject's eye that has been repeatedly acquired over a period including the transition from the first stimulating condition to the second stimulating condition. For example, the change information may be obtained based on a moving image acquired by repeatedly capturing tomographic images at a predetermined repetition frequency over a period including the transition from the first stimulating condition to the second stimulating condition.

EXPLANATION OF SYMBOLS

2 Ophthalmologic imaging apparatus
5L, 5R Body
10 Imaging optical system
30 Measurement optical system
30A Measurement driver
50 Visual target projection optical system
50A Visual target driver
60 Interference optical system
61 Light source unit
66 Galvanometer scanner
70B, 70C Reference driver
75 First reference mirror
77 Second reference mirror
79 Detector
80 Fixation optical system 100 Controller
110 Main controller
120 Storage
130A XYZ drive mechanism
130B Rotary drive mechanism
130C Optical axis deflection mechanism
150 Image forming unit
160 Data processor
161 Image area specifying unit
162 Change information acquisition unit
163 Optical property information acquisition unit
164 Intraocular distance calculator
165 Anterior eye change information acquisition unit
181 Display
182 Operation unit
O1 First optical axis
O2 Second optical axis
EL Subject's left eye
ER Subject's right eye

The invention claimed is:

1. An ophthalmologic imaging apparatus comprising:
a first optical system configured to apply at least a first accommodation stimulus and a second accommodation stimulus to a subject's eye by changing a view distance of the subject's eye to a visual target;
a tomographic image forming unit including a second optical system configured to split light from a light source into signal light and reference light, and detect interference light between the signal light having travelled via the subject's eye and the reference light, the tomographic image forming unit configured to create a tomographic image of the subject's eye based on a detection result of the interference light; and
an analyzer configured to compare a first tomographic image with a second tomographic image to acquire change information indicating a change in a predetermined tissue of the subject's eye due to a change of the accommodation stimulus, wherein the tomographic image forming unit is configured to create the first tomographic image of the subject's eye to which the first accommodation stimulus is being applied by the first optical system, and the second tomographic image of the subject's eye to which the second accommodation stimulus is being applied.

2. The ophthalmologic imaging apparatus of claim 1, wherein the analyzer includes
an image area specifying unit configured to analyze each of the first tomographic image and the second tomographic image to specify image areas corresponding to the predetermined tissue, and
a change information acquisition unit configured to compare the image area in the first tomographic image with the image area in the second tomographic image to acquire the change information indicating a change in morphology of the predetermined tissue.

3. The ophthalmologic imaging apparatus of claim 2, wherein the change information acquisition unit is configured to acquire the change information indicating a change in a shape of the predetermined tissue and/or density of tissues that constitute the predetermined tissue.

4. The ophthalmologic imaging apparatus of claim 3, wherein
the predetermined tissue includes a ciliary body,
the image area specifying unit is configured to specify ciliary body areas corresponding to the ciliary body as the image areas, and
the change information acquisition unit is configured to compare the ciliary body area in the first tomographic image with the ciliary body area in the second tomographic image to acquire the change information indicating a change in a shape of the ciliary body and/or a change in density of muscle fibers of the ciliary body.

5. The ophthalmologic imaging apparatus of claim 4, wherein, while an optical axis of the first optical system and an optical axis of the second optical system are oriented in different directions, the first optical system applies the accommodation stimulus to the subject's eye, and the second optical system detects the interference light.

6. The ophthalmologic imaging apparatus of claim 5, further comprising an optical system moving mechanism configured to relatively change direction of the optical axis of the first optical system and direction of the optical axis of the second optical system.

7. The ophthalmologic imaging apparatus of claim 2, wherein
the predetermined tissue includes a lens,
the image area specifying unit is configured to specify lens areas corresponding to the lens as the image areas, and
the change information acquisition unit is configured to compare the lens area in the first tomographic image and the lens area in the second tomographic image, to acquire the change information indicating a change in a shape of the lens.

8. The ophthalmologic imaging apparatus of claim 1, wherein the first optical system includes a pair of right and left optical systems configured to simultaneously apply the accommodation stimulus to subject's left eye and right eye.

9. The ophthalmologic imaging apparatus of claim 1, wherein the first optical system includes a measurement optical system configured to optically measure an optical property of the subject's eye.

10. The ophthalmologic imaging apparatus of claim 9, wherein
the measurement optical system is configured to measure the subject's eye to which the first accommodation stimulus is being applied to obtain a first measurement value of the optical property, and measure the subject's eye to which the second accommodation stimulus is being applied to obtain a second measurement value of the optical property, and
the analyzer includes an optical property information acquisition unit configured to acquire optical property information indicating a change in the optical property due to a change of the accommodation stimulus based on the first measurement value and the second measurement value.

11. The ophthalmologic imaging apparatus of claim 10, wherein
the measurement optical system is configured to measure refractive power of the subject's eye as the optical property, and
the optical property information acquisition unit is configured to acquire the optical property information indicating a change in an amount of accommodation of the subject's eye due to a change of the accommodation stimulus based on the first measurement value and the second measurement value of the refractive power.

12. The ophthalmologic imaging apparatus of claim 10, wherein
the measurement optical system is configured to measure aberration of the subject's eye as the optical property, and the optical property information acquisition unit is configured to acquire the optical property information indicating a change in the aberration of the subject's eye due to a change of the accommodation stimulus based on the first measurement value and the second measurement value of the aberration.

13. The ophthalmologic imaging apparatus of claim 1, wherein
the second optical system includes an optical path length changing unit configured to change optical path length of the signal light and/or the reference light,
the tomographic image forming unit is configured to acquire a tomographic image of a first site of the subject's eye and a tomographic image of a second site of the subject's eye, and
the analyzer includes an intraocular distance calculator configured to calculate a distance between the first site and the second site based on the optical path length when the tomographic image of the first site is acquired, and the optical path length when the tomographic image of the second site is acquired.

14. The ophthalmologic imaging apparatus of claim 13, wherein
the first site is an anterior surface of a cornea,
the second site is a surface of a fundus, and
the intraocular distance calculator is configured to calculate axial length of the subject's eye.

15. The ophthalmologic imaging apparatus of claim 1, wherein the analyzer includes an intraocular distance calculator configured to analyze one tomographic image of the subject's eye acquired by the tomographic image forming unit to calculate a distance between a first site and a second site depicted in this tomographic image.

16. The ophthalmologic imaging apparatus of claim 13, wherein
the first site is a posterior surface of a cornea,
the second site is an anterior surface of a lens, and
the intraocular distance calculator is configured to calculate anterior chamber depth of the subject's eye.

17. The ophthalmologic imaging apparatus of claim 1, wherein
the first optical system includes an imaging optical system configured to photograph an anterior segment of the subject's eye, and
the analyzer is configured to compare a first anterior eye image with a second anterior eye image to acquire anterior eye change information indicating a change in a predetermined tissue of the anterior segment due to a change of the accommodation stimulus, wherein the imaging optical system is configured to capture a first anterior eye image of the subject's eye to which the first accommodation stimulus is being applied, and a second anterior eye image of the subject's eye to which the second accommodation stimulus is being applied.

18. An ophthalmologic imaging apparatus comprising:
a stimulating unit configured to apply at least a first accommodation stimulus and a second accommodation stimulus to a subject's eye by changing a view distance of the subject's eye to a visual target;
a tomographic image forming unit including an optical system configured to split light from a light source into signal light and reference light, and detect interference light between the signal light having travelled via the subject's eye and the reference light, the tomographic image forming unit configured to create a tomographic image of the subject's eye based on a detection result of the interference light; and
an analyzer configured to compare a first tomographic image with a second tomographic image to acquire change information indicating a change in a predetermined tissue of the subject's eye due to a change of the accommodation stimulus, wherein the tomographic image forming unit is configured to create the first tomographic image of the subject's eye to which the first stimulus is being applied by the stimulating unit, and the second tomographic image of the subject's eye to which the second stimulus is being applied.

19. The ophthalmologic imaging apparatus of claim 15, wherein
the first site is a posterior surface of a cornea,
the second site is an anterior surface of a lens, and
the intraocular distance calculator is configured to calculate anterior chamber depth of the subject's eye.

* * * * *